US012740970B2

(12) United States Patent
Yasuzawa

(10) Patent No.: US 12,740,970 B2
(45) Date of Patent: Sep. 22, 2026

(54) RAPAMYCIN-CONTAINING PHARMACEUTICAL COMPOSITION

(71) Applicant: NOBELPHARMA CO., LTD., Tokyo (JP)

(72) Inventor: Toru Yasuzawa, Tokyo (JP)

(73) Assignee: Nobelpharma Co., Ltd., Tokyo (JP)

( * ) Notice: Subject to any disclaimer, the term of this patent is extended or adjusted under 35 U.S.C. 154(b) by 595 days.

(21) Appl. No.: 18/456,135

(22) Filed: Aug. 25, 2023

(65) Prior Publication Data

US 2025/0032463 A1 Jan. 30, 2025

(30) Foreign Application Priority Data

Jul. 27, 2023 (DE) ......................... 102023119976.5

(51) Int. Cl.

*A61K 31/436* (2006.01)
*A61K 9/06* (2006.01)
*A61K 47/18* (2017.01)
*A61K 47/30* (2006.01)

(52) U.S. Cl.

CPC .............. *A61K 31/436* (2013.01); *A61K 9/06* (2013.01); *A61K 47/18* (2013.01); *A61K 47/30* (2013.01)

(58) Field of Classification Search

CPC .................................................. A61K 31/436
See application file for complete search history.

(56) References Cited

U.S. PATENT DOCUMENTS 6,605,613 B2 8/2003 Navarro et al.
6,852,729 B2 2/2005 Navarro et al.
7,297,703 B2 11/2007 Navarro et al.
7,572,804 B2 8/2009 Navarro et al.

FOREIGN PATENT DOCUMENTS

JP 3805625 B2 8/2006

OTHER PUBLICATIONS

Balestri, et al., "Analysis of current data on the use of topical rapamycin in the treatment of facial angiofibromas in Tuberous Sclerosis Complex", JEADV 2015, 29, pp. 14-20.

*Primary Examiner* — Golam M Shameem
(74) *Attorney, Agent, or Firm* — Sughrue Mion, PLLC

(57) ABSTRACT

The present invention relates to a stable rapamycin-containing composition for treating skin diseases, a method of producing the same, a method of stabilizing the same, and a method of inhibiting the degradation of rapamycin.

4 Claims, 1 Drawing Sheet

RAPAMYCIN-CONTAINING PHARMACEUTICAL COMPOSITION

TECHNICAL FIELD

The present invention relates to a stable rapamycin-containing composition for treating skin diseases, a method of producing the same, and a method of stabilizing the same. Further, the invention relates to a method of inhibiting degradation of rapamycin in the rapamycin-containing composition for treating skin diseases.

The present invention also relates to a technique for improving the transdermal absorption of the rapamycin-containing composition for treating skin diseases. Specifically, the invention relates to a composition for treating skin diseases (gel formulation) in which transdermal absorption of the active ingredient, rapamycin, is improved by adjusting the concentration of ethanol contained in the composition to a specific range, a method of improving the transdermal absorption of a rapamycin-containing composition for treating skin diseases, and a method of producing a rapamycin-containing composition for treating skin diseases in which the transdermal absorption of rapamycin is improved.

BACKGROUND ART

Rapamycin (generic name: sirolimus), a metabolite of the actinomycete *Streptomyces hygroscopicus*, is known to inhibit the action of mammalian target of rapamycin (mTOR), which regulates cell division, growth, and survival. It is known that mTOR is permanently activated in various diseases such as Tuberous Sclerosis Complex (TSC), and rapamycin may be used as a therapeutic agent for these diseases by inhibiting the action of mTOR. Rapamycin may be used as a therapeutic agent for these diseases by inhibiting the action of mTOR (R. Balestri et al., Journal of the European Academy of Dermatology and Venereology, 2015, vol. 29, pp. 14-20).

TSC is associated with angiofibromas and other skin diseases, and topical application of rapamycin to the affected area is an effective way to treat TSC with minimal side effects. It is necessary to combine rapamycin dissolved in a solvent with a base material such as a gel or ointment to use rapamycin in a topical application. However, rapamycin is unstable in aqueous solvents.

In addition, as a stabilization technique, a technique is disclosed in which an antioxidant is added to an inert solvent solution to precipitate the mixture to improve the stability of a rapamycin derivative (40-O-(2-hydroxy)ethyl-rapamycin) to oxygen during the isolation process (JP Patent No. 3805625).

SUMMARY OF INVENTION

Technical Problem

An objective of the present invention is to provide a stable rapamycin-containing composition for treating skin diseases (gel formulation), a method of producing the same, and a method of stabilizing the same. Another objective of the present invention is to provide a method of inhibiting degradation of rapamycin in the rapamycin-containing composition for treating skin diseases. Yet another objective of the present invention is to provide a method of stabilizing the rapamycin-containing composition for treating skin diseases and a method of inhibiting its degradation.

On the other hand, in compositions for the treatment of skin diseases as topical formulations, it is important that the active ingredient, rapamycin, be sufficiently absorbed through the skin to reach the affected area. Until now, conditions for improving this transdermal absorption have not been disclosed.

The present invention was achieved in view of the above circumstances, and is to provide a rapamycin-containing composition for treating skin diseases (gel formulation) with improved transdermal absorption. It is also an objective of the present invention to provide a method of improving the transdermal absorption of a rapamycin-containing composition for treating skin diseases.

Solution of Problem

The present invention relates to a method of producing a rapamycin-containing composition for treating skin diseases, which comprises the steps of dissolving rapamycin in an ethanol-containing solvent, adding a gelling and/or thickening agent to the resulting rapamycin-containing solution, and adjusting the pH of the resulting rapamycin-containing composition to 5.5 to 6.1.

The method of producing a rapamycin-containing composition for treating skin diseases, in one embodiment, includes the step of adjusting the pH of the final composition in a range of about 5.5 to about 6.1. Such a process may inhibit the degradation of the main active pharmaceutical ingredient, rapamycin, and improve its stability. Various studies have been conducted to stabilize rapamycin-containing compositions, but conditions sufficient to achieve the desired effect had not been found. The inventor has found that the composition containing rapamycin can be stabilized by a simple method such as controlling pH within a certain range and achieved the present invention.

The method of producing a rapamycin-containing composition for treating skin diseases, in one embodiment, includes mixing rapamycin, and ethanol in an amount that results in a concentration of 40-50% by weight in the composition. Such a process may improve the transdermal absorption of rapamycin-containing composition for treating skin diseases.

Since rapamycin is almost insoluble in water, when it was blended in gel formulations, rapamycin was dissolved in a solvent such as ethanol in advance and mixed with the base agent. That means, in gel formulations containing rapamycin, the ethanol contained is only a necessary ingredient for dissolving the rapamycin, and no studies have been conducted to examine conditions focusing on the relationship between the ethanol contained and the transdermal absorption of the active ingredient. The inventor found that the transdermal absorption of rapamycin can be improved by adjusting the ethanol concentration in the gel formulation within a certain range, and completed the present invention.

The present invention relates to a method of stabilizing the rapamycin-containing composition for treating skin diseases comprising the step of adjusting the pH of the composition in a range of about 5.5 to about 6.1.

Further, the present invention relates to a method of inhibiting degradation of rapamycin in the rapamycin-containing composition for treating skin diseases comprising the step of adjusting the pH of the composition in a range of about 5.5 to about 6.1.

The rapamycin-containing composition for treating skin diseases of the present invention comprises, in one embodiment, rapamycin; and at least one pH adjuster selected from the group consisting of sodium hydroxide, sodium bicarbonate, triethanolamine, tris-hydroxymethylaminomethane; and to be a rapamycin-containing composition for treating skin diseases having pH of from about 5.5 to about 6.1.

The rapamycin-containing composition for treating skin diseases of the present invention comprises, in one embodiment, rapamycin and ethanol; and to be a rapamycin-containing composition for treating skin diseases with the amount of ethanol is in a range of 40-50% by weight with respect to the composition. Such a structure can improve the transdermal absorption of rapamycin.

Advantageous Effects of Invention

The present invention may provide a rapamycin-containing composition for treating skin diseases with reduced degradation of rapamycin and stability.

The present invention may also provide a rapamycin-containing composition for treating skin diseases with improved transdermal absorption.

DESCRIPTION OF EMBODIMENTS

Figure 1:
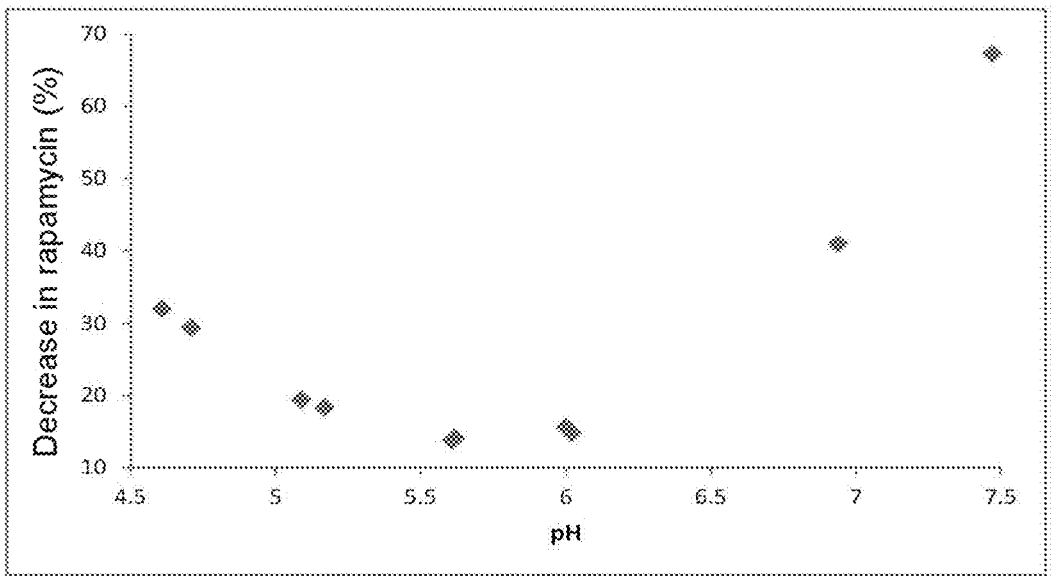
FIG. 1 The graph shows the decomposition inhibitory effect (stabilizing effect) of rapamycin. A remarkable decomposition inhibitory effect is observed only when the pH is about 5.5 to 6.1.

The invention is described in detail below.

The method of producing a rapamycin-containing composition for treating skin diseases of the present invention includes, in one embodiment, the steps of dissolving rapamycin in an ethanol-containing solvent, adding a gelling agent and/or thickening agent to the resulting rapamycin-containing solution, and adjusting the pH of the resulting rapamycin-containing composition from about 5.5 to about 6.1.

Examples of gelling agents added to the rapamycin-containing solution include water-soluble cellulose-derived polymers, such as hydroxymethyl cellulose, hydroxyethyl cellulose, hydroxypropyl cellulose and hydroxypropyl methyl cellulose, carboxymethyl cellulose, methyl hydroxyethyl cellulose, methyl cellulose, and carrageenan. Examples of the thickening agents include carboxy vinyl polymer and hydroxypropyl cellulose. These may be used alone or in combination.

The pH may be adjusted by adding conventional pH adjusters such as basic additives, acidic additives, additives with buffering effects (buffers), or inorganic salts. Such pH adjusters include basic additives such as sodium hydroxide and sodium bicarbonate; acidic additives such as hydrochloric acid, sulfuric acid, phosphoric acid, citric acid, tartaric acid, malic acid, mesyl acid, tosyl acid, besyl acid; buffers such as triethanolamine, tris-hydroxymethylamino methane, 2-morpholinoethanesulfonic acid, alkaline metal salts, alkaline earth metal salts, and ammonium salts. The inorganic salts include calcium chloride, sodium chloride, calcium oxide, and magnesium sulfate.

The pH adjusters include, but not limited to, various substances such as those mentioned above. For example, when the composition contains gelling or thickening agents having a carboxylic acid, preferable pH adjusters include at least one selected from the group consisting of sodium hydroxide, potassium hydroxide, ammonium hydroxide, sodium bicarbonate, triethanolamine, tris-hydroxymethylaminomethane, and 2-morpholinoethanesulfonic acid.

The method of producing a rapamycin-containing composition for treating skin diseases of the present invention, in one embodiment, includes the step of mixing rapamycin, and ethanol in an amount that results in a concentration of 40-50% by weight in the composition. Specific examples include as follows.

First, dissolve rapamycin by mixing it with ethanol in an amount that will result in a concentration of 40-50% by weight in the final composition, and add a solvent such as purified water. Then, a gelling agent or thickening agent, such as carboxy vinyl polymer, is added, and if necessary, excipients or additives are added and stirred to swell the gelling agent/thickening agent sufficiently and homogenize the mixture, and the pH is adjusted by adding the pH adjuster mentioned above. The rapamycin-containing composition can be resulting as a gel formulation by adding the above-mentioned pH adjuster and adjusting the pH.

The method of stabilizing the rapamycin-containing composition for treating skin diseases of the present invention includes the step of adjusting the pH of the composition in a range of about 5.5 to about 6.1. The pH adjustments and substances to adjust the pH are as described above.

Further, the method of stabilizing a rapamycin-containing composition for treating skin diseases of the present invention may include the steps of dissolving rapamycin in an ethanol-containing solvent, and adding a gelling agent and/or thickening agent to the resulting rapamycin-containing solution. The gelling agent and thickening agent to be added to the rapamycin-containing solution are as described above.

The method of inhibiting degradation of the rapamycin-containing composition for treating skin diseases of the present invention includes the step of adjusting the pH of the composition in a range of about 5.5 to about 6.1. The pH adjustments and substances to adjust the pH are as described above.

The method of inhibiting degradation of rapamycin in the rapamycin-containing composition for treating skin diseases of the present invention may further include the steps of dissolving rapamycin in an ethanol-containing solvent, and adding a gelling and/or thickening agent to the resulting rapamycin-containing solution. Here, gelling agents and thickening agents added to the rapamycin solution are as described above.

A rapamycin-containing composition for treating skin diseases (hereinafter "the rapamycin-containing composition") of the present invention comprises (i) rapamycin, (ii) carboxylic acid-containing aqueous polymer, and (iii) at least one pH adjuster selected from the group consisting of sodium hydroxide, potassium hydroxide, ammonium hydroxide, sodium bicarbonate, triethanolamine, trihydroxymethylaminomethane, and 2-morpholinoethanesulfonic acid, wherein pH is in a range of about 5.5 to about 6.1.

Here, carboxylic acid-containing aqueous polymers can be at least one selected from the group consisting of carboxy vinyl polymer, carboxymethyl cellulose, and carboxyethyl cellulose, alone or in combination.

The method of improving the transdermal absorption of a rapamycin-containing composition for treating skin diseases is characterized in that the concentration of ethanol in said composition is about 40 to about 50%. As explained in the examples below with reference to experimental data, the inventors have shown for the first time that the transdermal absorption of rapamycin is improved when the ethanol concentration in the composition is about 40 to about 50%. Improved transdermal absorption in compositions for the treatment of skin diseases, which are topical products, indicates that the active ingredients can reach the affected area more efficiently. Thus, the present invention can improve the therapeutic efficacy of a rapamycin-containing composition for treating skin diseases.

The content of rapamycin in the rapamycin-containing composition of the present invention is not particularly limited, but can be, for example, from 0.05 to 3% by weight of the total composition, preferably from 0.1 to 2% by weight, more preferably from 0.1 to 0.5% by weight.

The content of the pH adjuster in the rapamycin-containing composition of the present invention is not particularly limited as long as the pH of the composition can be adjusted to about 5.5 to about 6.1. Furthermore, the content of such a pH adjuster can be selected according to the type of pH adjuster used.

The rapamycin-containing composition of the present invention may include at least one selected from the group consisting of excipients, additives, and solvents, normally used to form pharmaceutical dosage forms to the extent that they do not interfere with the effects of the invention. Such agents and solvents can be used, for example, gelling agents, thickening agents, inorganic salts, ethanol, and water. The above-mentioned gelling agents, thickening agents, and inorganic salts can be used.

Further, other active ingredients can be added to the rapamycin-containing composition of the present invention as long as they do not interfere with the effect of rapamycin, the main active ingredient. Such other active ingredients may include, for example, tacrolimus and steroids.

The rapamycin-containing composition of the present invention can be prepared in optimal dosage forms, such as, for example, cream, paste, jelly, gel, emulsion, and liquid. For example, when prepared into ointments, liniments, lotions, etc., in addition to the other excipients or additives mentioned above, at least one selected from the following can be added as needed: sodium alginate; polymers such as gelatin, cornstarch, tragacanth gum, methylcellulose, hydroxyethylcellulose, carboxymethylcellulose, xanthan gum, dextrin, carboxymethyl starch, polyvinyl alcohol, sodium polyacrylate, methoxyethylene-polymers such as maleic anhydride copolymer, polyvinyl ether, and polyvinyl pyrrolidone; oils such as beeswax, olive oil, cocoa oil, sesame oil, soybean oil, *Camellia* oil, peanut oil, bovine oil, pig oil, and lanolin; vaselines such as white vaseline and yellow vaseline; paraffin, mixtures of liquid paraffin and polyethylene (gelling hydrocarbons); stearic acid; lauryl esters, myristate esters, octanoate esters; cetyl alcohol, stearyl alcohol; polyethylene glycol; dimethyl sulfoxide, dodecyl pyrrolidone; urea; eizon; kaolin, bentonite, zinc oxide, titanium dioxide.

The rapamycin-containing composition of the present invention may be produced by, for example, the following procedures.

First, dissolve rapamycin in ethanol and add a solvent such as purified water. Then, a gelling agent or thickening agent, such as carboxy vinyl polymer, is added, and if necessary, excipients or additives are added and stirred and mixed to sufficiently swell the gelling agent or thickening agent and to homogenize the mixture. The pH of the system is then adjusted to about 5.5 to about 6.1 by adding a pH adjuster.

The rapamycin-containing composition of the present invention has immunosuppressive properties, so may be used, for example, to treat immune-related skin diseases.

Examples of specific skin diseases include dermatitis, contact dermatitis, psoriasis, atopic dermatitis, seborrheic dermatitis, nummular eczema, vitiligo, keloids, autosensitized dermatitis, stasis dermatitis, sebaceous deficiency eczema, skin tumors of tuberous sclerosis, and skin tumors of Recklinghausen's disease.

The dosage of pharmaceutical products using the rapamycin-containing composition of the present invention can be modified according to the patient's gender, age, physiological condition, pathological state, and other factors. For example, when used as a topical application, 0.01 to 100 $mg/m^2$ (body surface area) of rapamycin per adult per day can be administered by topical application.

EXAMPLES

Although the invention is described below with specific embodiments, it is understood that the invention is not limited to those embodiments and that various changes and modifications in them may be made by those skilled in the art without departing from the scope or intent of the invention as set forth in the appended claims.

Example 1

Gel formulations were prepared by mixing each of the ingredients listed in Table 1 in the content listed in Table 1, and the pH was measured. All the formulation samples were clear and colorless gel.

TABLE 1

Composition and content of each formula (% by weight)

| Ingredients | Formula 1 | Formula 2 | Formula 3 | Formula 4 | Formula 5 | Formula 6 | Formula 7 | Formula 8 | Formula 9 | Formula 10 |
|---|---|---|---|---|---|---|---|---|---|---|
| rapamycin | 0.2 | 0.2 | 0.2 | 0.2 | 0.2 | 0.2 | 0.2 | 0.2 | 0.2 | 0.2 |
| carboxy vinyl polymer | 1 | 1 | 1 | 1 | 1 | 1 | 1 | 1 | 1 | 1 |
| ethanol | 49.42 | 49.62 | 49.71 | 49.76 | 49.5 | 49.64 | 49.72 | 49.77 | 48.8 | 48.3 |
| triethanolamine | 0.38 | 0.18 | 0.09 | 0.04 | — | — | — | — | 1 | 1.5 |
| tris-hydroxymethyl aminomethane | — | — | — | — | 0.3 | 0.16 | 0.08 | 0.035 | — | — |
| water | 49 | 49 | 49 | 49 | 49 | 49 | 49 | 49 | 49 | 49 |
| Total | 100 | 100 | 100 | 100 | 100 | 100 | 100 | 100 | 100 | 100 |
| pH at preparation | 6.02 | 5.62 | 5.09 | 4.61 | 6 | 5.61 | 5.17 | 4.71 | 6.94 | 7.47 |

About 50 g of the gel formulation sample prepared according to each formula was filled into 50-mL glass vials and capped with a PP lid. Each vial was stored in the dark at 50° C. for 7 days. Rapamycin was quantified by HPLC at the start of the study and after storage using the following conditions.

HPLC Conditions:

Detector: UV absorbance spectrophotometer (measurement wavelength: 278 nm)

Column: Stainless steel tube with an inner diameter of 4.6 mm and a length of 25 cm packed with 5 μm octadecylsilylated silica gel for HPLC Column temperature: constant temperature around 40° C.

Mobile phase: acetonitrile/water mixture (13:7)

Flow rate: 0.8 mL/min

Based on the quantification results, the amount of decrease in rapamycin was calculated with the starting time of the test as 100, and the stability of each formula was evaluated.

The results are shown in FIG. 1. As shown in the figure, both too high and too low pH reduced the stability of rapamycin, with the degradation of rapamycin being most inhibited when the pH was about 5.5 to about 6.1 or about 5.6 to about 6.0. No difference in effect on stability was observed between the two pH adjusters (triethanolamine and tris-hydroxymethylaminomethane). These results indicated that the inhibitory effect of rapamycin on degradation was mainly due to the pH being adjusted around about 5.5 to about 6.1 or around about 5.6 to about 6.0.

These results confirmed that a pH range of about 5.5 to about 6.1 or about 5.6 to about 6.0 can suppress the decrease of rapamycin during storage, and improve the stability of rapamycin in the rapamycin-containing composition (gel formulation).

Example 2

(1) Sample Preparation

Gel formulations were prepared by mixing each of the ingredients listed in Table 2 in the content listed in Table 2.

TABLE 2

| Composition and content of each formula (% by weight) | | | | | | | | | |
|---|---|---|---|---|---|---|---|---|---|
| Ingredients | Formula 1 | Formula 2 | Formula 3 | Formula 4 | Formula 5 | Formula 6 | Formula 7 | Formula 8 | Formula 9 |
| rapamycin | 0.1 | 0.2 | 0.1 | 0.2 | 0.2 | 0.2 | 0.2 | 0.2 | 0.2 |
| carboxy vinyl polymer | 1.0 | 1.0 | 1.0 | 1.0 | 1.0 | 1.0 | 1.0 | 1.0 | 1.0 |
| ethanol | 20.00 | 20.00 | 30.00 | 30.00 | 30.00 | 30.00 | 40.00 | 49.42 | 49.42 |
| triethanolamine | 0.38 | 0.38 | 0.38 | 0.38 | 0.38 | 0.38 | 0.38 | 0.38 | 0.38 |
| 1,3-butylene glycol | 5.0 | 5.0 | 5.0 | | 5.0 | 5.0 | 5.0 | 5.0 | |
| water | 73.52 | 73.42 | 63.52 | 68.42 | 63.42 | 63.42 | 53.42 | 44.00 | 49.00 |

(2) Transdermal Absorption Study Using Cultured Human Skin Cells

A commercially available model of human skin reconstruction (Product name: TESTSKIN LSE-high, manufactured by Toyobo Co.) was used.

The transwell with attached cultured tissue were removed from the transport medium, and the attached assay ring (10 mm inner diameter) was attached to a uniformly thick area at the top of the cultured tissue. Approximately 100 mg of the test substance was uniformly applied to the surface of the cultured tissue inside the assay ring and incubated for 24 hours in an incubator set at 37° C. and 5% CO2. After incubation, the test substance on the surface was carefully removed so as not to damage the cells. The cells were then cut into 8 mm diameter circles, and the epidermis and support layer (polycarbonate layer for attaching the cultured tissue) were removed to make a dermis layer sample. To the collected dermis layer sample, 1 mL of methanol was added and stirred vigorously to extract the osmotic component. The extract was subjected to LC/MS/MS under the following conditions to quantify rapamycin in the dermis layer. The quantitative value of rapamycin was used to evaluate the transdermal absorption of rapamycin in each sample.

HPLC Conditions:

Detector: UV absorbance spectrophotometer (measurement wavelength: 278 nm)

Column: Stainless steel tube with an inner diameter of 4.6 mm and a length of 150 mm packed with 5 μm octadecylsilylated silica gel for HPLC Column temperature: constant temperature around 50° C.

Mobile phase: 5 mmol/L ammonium formate containing 0.1 vol % formic acid and acetonitrile, mixed at a ratio of 10:90

Flow rate: 0.8 mL/min

MS/MS Conditions:

Ionization mode: ESI-Positive method

Scanning type: MRM

Monitoring ion: Rapamycin

Figure 2:
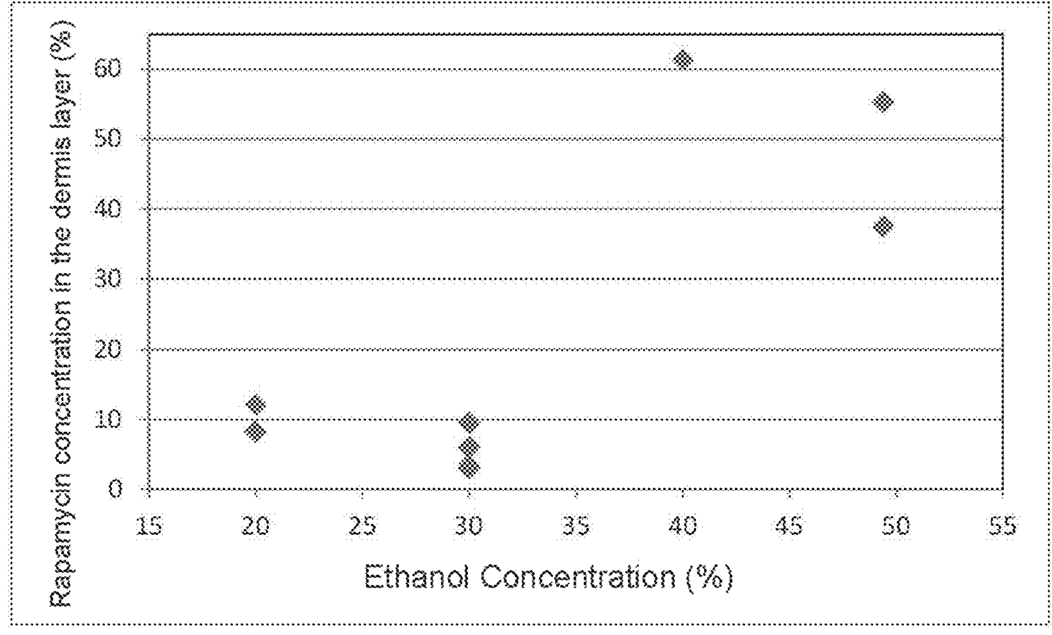
FIG. 2 The graph shows the ethanol concentration in the composition and the transdermal absorption of rapamycin. It is observed that the concentration of rapamycin in the dermis is higher and its transdermal absorption is improved when the ethanol concentration is in a range of approximately 40-50% by weight.

The relationship between the ethanol content in each sample and the concentration of rapamycin in the dermis layer is shown in FIG. 2. As shown in the figure, the concentration of rapamycin in the dermis layer increased dramatically at around 40% ethanol concentration. In other words, at least 40-50% ethanol in the composition improves the transdermal absorption of rapamycin.

The above mentioned results indicate that the ethanol concentration of 40-50% in the rapamycin-containing compositions improves the transdermal absorption of rapamycin and provides compositions useful as compositions for treating skin diseases.

INDUSTRIAL APPLICABILITY

The present invention may provide a rapamycin-containing composition for treating skin diseases with reduced degradation of rapamycin and improved stability, thereby make it possible to provide a more effective agent for treating skin diseases.

The present invention may also provide a rapamycin-containing composition for treating skin diseases with improved transdermal absorption, thereby make it possible to provide a more effective agent for treating skin diseases.

The invention claimed is:

1. A method of producing a rapamycin-containing composition for treating skin diseases, which comprises the steps of dissolving rapamycin in an ethanol-containing solvent, adding a gelling and/or thickening agent to the resulting rapamycin-containing solution, and adjusting the pH of the resulting rapamycin-containing composition to 5.5 to 6.1 with triethanolamine or tris hydroxymethyl aminomethane.

2. A method of inhibiting degradation of rapamycin in the rapamycin-containing composition for treating skin diseases, wherein the method comprises the step of adjusting the pH of the resulting rapamycin-containing composition to 5.5 to 6.1 with triethanolamine or tris hydroxymethyl aminomethane.

3. The method according to claim 2, further comprising the steps of dissolving rapamycin in an ethanol-containing solvent, and adding a gelling and/or thickening agent to the resulting rapamycin-containing solution.

4. A rapamycin-containing composition for treating skin diseases comprising (i) rapamycin, (ii) carboxylic acid-containing aqueous polymer, and (iii) at least one pH adjuster selected from triethanolamine and tris-hydroxymethylaminomethane, having a pH of 5.5 to 6.1.

* * * * *